United States Patent [19]

Gross et al.

[11] Patent Number: 4,534,647
[45] Date of Patent: Aug. 13, 1985

[54] APPARATUS FOR PHOTOMETRICALLY SCANNING GELS

[75] Inventors: Valery N. Gross; Vyacheslav D. Stupnik, both of Alma-Ata, U.S.S.R.

[73] Assignee: Institut Molekulyarnoi Biologii Biokhimii Akademii Nauk Kazakhskoi SSR, Alma-Ata, U.S.S.R.

[21] Appl. No.: 438,868

[22] PCT Filed: Feb. 23, 1981

[86] PCT No.: PCT/SU81/00015
§ 371 Date: Oct. 18, 1982
§ 102(e) Date: Oct. 18, 1982

[87] PCT Pub. No.: WO82/02946
PCT Pub. Date: Sep. 2, 1982

[51] Int. Cl.³ ............ C25B 9/00; G01J 1/04; G01N 21/03; G01N 27/26
[52] U.S. Cl. .................... 356/344; 356/440; 204/299 R
[58] Field of Search ........... 356/344, 440, 436, 244; 204/299 R

[56] References Cited

U.S. PATENT DOCUMENTS 3,994,593 11/1976 Kato et al. ............ 356/444
4,427,294 1/1984 Nardo .................. 356/344

FOREIGN PATENT DOCUMENTS 1376245 of 0000 United Kingdom .

OTHER PUBLICATIONS cf. G. Maurer. Disc-Electrophoresis (in Russian), 1971, MIR Publishing House, Moscow, pp. 103–104, FIG. 29.
cf. Booklet ISCO (Instruments Specialities Company), USA, Lincoln, Nebraska, "Instruments with a Difference", pp. 20–21, May, 1979.
Prospect of the ISCO Company, issued Jan. 1978, (Instruments with a Difference Photometric Gel Scanner", pp. 56–57.
"Metodi Issledovanii v Immunologii", edited by Lefkovits J. and Pernis B., approved to publication 1981 (Mir, Moscow), pp. 102, 104, 114.

Primary Examiner—R. A. Rosenberger
Assistant Examiner—Michael F. Vollero
Attorney, Agent, or Firm—Lilling & Greenspan

[57] ABSTRACT

An apparatus for photometrically scanning gels comprises a monochromator from which the light beam passes through a stop aperture and a gel placed in a cell, which are installed one after the other along the path of the light beam. The cell is caused to move relative to the light beam by means of a drive and the light is received by a photometer. The cell is made in the form of two superposed discs each having on one side congruent grooves which define at least one compartment for placing the gels therein when the discs are superposed on one another.

5 Claims, 5 Drawing Figures

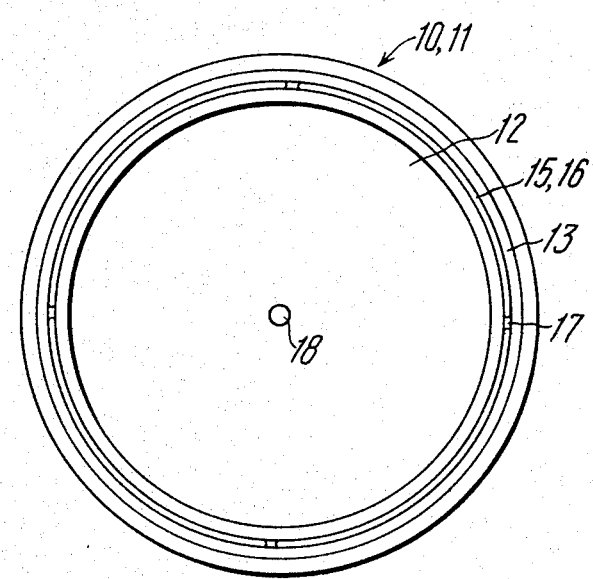
FIG. 2
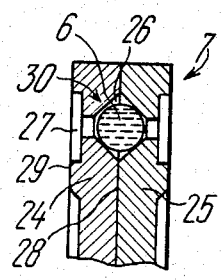
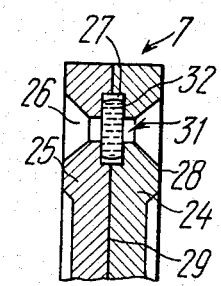
FIG. 4  FIG. 5

APPARATUS FOR PHOTOMETRICALLY SCANNING GELS

FIELD OF THE INVENTION

The invention relates to photometric equipment and, more particularly, it deals with apparatus for photometrically scanning gels obtained as a result of the electrophoretic analysis.

BACKGROUND OF THE INVENTION

The method of electrophoretic analysis of biological preparations in gels is one of the main areas of biochemical, medical and selection studies.

The widespread application of the method is due not only to its high resolution, simplicity and low cost of necessary equipment, but also to the possibility of effecting parallel analysis of a large number (several scores) of biological preparations. This imposes more stringent requirements on apparatus for photometrically scanning gels, in particular, on the productivity, cost, compactness and possibility of ensuring high measurement accuracy.

In addition, the trend to improve the method of electrophoretic analysis of biological preparations in gels with the aim of increasing the gel length has recently become obvious as this would enable the achievement of maximum efficiency of the analysis—maximum separation of preparations of complicated composition. The development of apparatus for photometrically scanning such gels which are up to 40–50 cm long requires the application of radically new technical concepts because conventional apparatus used for such purpose would be unwieldy (up to 100–120 cm long) which is due, among other things, to considerable difficulties in providing for uniform translational motion of gels during scanning thus resulting in a more complicated design and higher cost.

DESCRIPTION OF THE PRIOR ART

Known in the art is an apparatus for photometrically scanning gels, comprising a monochromator from which the light beam passes, through a stop aperture and a gel placed in a cell which are installed one after the other along the light beam path, the cell being caused to move relative to the light beam by means of a manual drive having a micrometric gearing, and the light being received by a photometer (cf. G. Maurer. Disc-Electrophoresis (in Russian), 1971, MIR Publishing House, Moscow, pp.103–104, FIG. 29).

In this apparatus, the cell is made in the form of a quartz tube of a constant diameter which is caused to reciprocate by means of a manual drive.

As the quartz tube in this apparatus is 7 cm long, only one gel may be placed in the tube. This requires frequent recharging of the cell, hence the productivity is low.

The use of expensive quartz tubes in the apparatus makes it rather costly. For photometrically scanning gels of different diameters, it is necessary to have a set of quartz tubes of respective diameters which considerably raises the cost of such an apparatus. In case a single quartz tube is used for studying gels of different diameters, deformation of gels when placed in the tube or a loose accommodation of the gel in the tube make errors in scanning more likely.

In addition, the use of the manual drive for moving the cell in this apparatus results in a low productivity in scanning gels and in high probability of errors in performing multiple repeated operations of moving the cell through one and the same distance read from the micrometric vernier.

An apparatus for photometrically scanning gels has been proposed, comprising a monochromator from which the light beam passes through a stop aperture and a gel placed in a cell which are installed one after the other on the light beam path, the cell being caused to move relative to the light beam by an electromechanical drive and the light being received by a photometer (cf. Booklet ISCo (instruments Specialities Company), USA, Lincoln, Neb., "instruments with a difference", pp.20–21, May, 1979).

In this apparatus, the cell comprises a quartz tube 25 cm long installed for reciprocations relative to the light beam under the action of an electromechanical drive.

The use of the quartz tube 25 cm long, which makes it possible to scan two gels 12 cm long without recharging, and the provision of the electromechanical drive enable a higher productivity and smaller probability of error in scanning gels, compared to the abovedescribed apparatus. But the increase in the productivity is yet insufficient for mass-scale analysis operations. Further increase in the cell length cannot bring a solution to the problem since this is associated with problems of the manufacture and operation of rather long quartz tubes which should exhibit uniform optical properties over the whole length. An additional difficulty in improving this apparatus, which is also associated with the cell being made in the form of the quartz tube, is the complicated design of the reciprocatory drive for moving a very long cell. Moreover, the use of expensive quartz tubes as the cells does not permit lowering the cost of the apparatus of this type.

A large length of quartz tube in this apparatus makes the reciprocatory drive very complicated, thus resulting in a rather sophisticated design of the apparatus as a whole.

The apparaatus is also large in size as for an accurate movement of the cell 25 cm long the apparatus is provided with a reciprocatory drive which is 50 cm long. In conducting biochemical and medical tests, the compactness of such apparatus is very important as a large number of the apparatus are used even for only one type of analysis.

As distinguished from the abovedescribed apparatus, this apparatus makes it possible to scan both cylindrical and prismatic gels. However, as the cells in this apparatus are of predetermined dimensions, the range of cross-sectional dimensions of the gels is restricted which makes it difficult to use the apparatus for scanning electrophoretic patterns obtained in various types of electrophoretic analysis. This results in limited operational capabilities of the apparatus which is now becoming a great disadvantage in analytical studies using gels.

In this apparatus, similarly to that described above, a strong diffusion of light by the cylindrical surfaces of the gels and cell cannot be eliminated. In addition, damage to the gel surface is recorded as a false peak. This results in the absence of improvement of the measurement accuracy in this apparatus compared to the abovedescribed apparatus, the errors being associated with the negative influence of light diffusion and surface damages to the gel on the scanning results.

In both abovedescribed apparatus errors associated with nonuniform position of gels or their loose accommodation in the cell cannot be eliminated.

SUMMARY OF THE INVENTION

The invention is based on providing a simple and compact apparatus for photometrically scanning gels, in which the cell for the accommodation of gels is made in such a manner as to provide for a substantial improvement of the gel scanning productivity and measurement accuracy, to lower the cost and to improve the operational capabilities of the apparatus.

This is achieved by an apparatus for photometrically scanning gels, comprising a monochromator from which the light beam passes through a stop aperture and a gel placed in a cell, which are installed one after the other along the light beam path. The cell is caused to move under the action of an electromechanical drive and the light is received by a photometer. According to the invention, the cell comprises two superposed discs each having on at least one side thereof congruent grooves which define at least one compartment for placing gel therein when the discs are superposed on one another.

Apertures are preferably made in both discs of the cell on the groove bottom side for the passage of the light beam.

This construction of the apparatus according to the invention makes it possible to improve the productivity of scanning owing to the reduction of the total number of auxiliary operations associated with charging the cell with gels and with installation of the cell in the apparatus. Placing several gels into the cell makes it possible to conduct scanning for a longer time period during which the operator may attend to other operations. The time for placing several (e.g., four) gels in the apparatus according to the invention is substantially equal to the time needed for placing one gel in the abovedescribed prior art apparatus.

In addition, the provision of the cell in the form of two discs having congruent grooves makes it possible to improve the accuracy of measurement owing to the possibility of uniform accommodation of gels in the cell provided by the design of the cell thus preventing axial deformation of gels, and an exactly reproducible position of the gels during scanning is ensured. For this reason, scanning gels in the apparatus according to the invention enables high reproducibility of results and an accuracy which is constant for all measurements. This is very important as it is crucial for the gel analyses to have the possibility of quantitative comparison.

In addition, this construction of the cell makes it possible to avoid the need for using quartz tubes, thus lowering the cost of the apparatus.

A substantial increase in the working length of the cell compartments defined by congruent grooves in the cell discs makes it possible to scan gels of a large length thus considerably improving the operational capabilities of the apparatus. Moreover, the capabilities of the apparatus are also improved by the cell being made in the form of two discs having congruent grooves. This facility makes it possible to scan gels of different diameters, so that the apparatus may be used for scanning electrophoretic patterns obtained as a result of various types of electrophoretic analysis in gels.

The structural embodiment of the cell according to the invention enables a substantial reduction of the size of the apparatus for scanning gels, whereby the cell dimension which determines the size of the apparatus as a whole is three times as small as the working length of the cell compartment.

In case grooves are made on either side of each disc of the cell in the apparatus according to the invention, the grooves made on the other side of the discs may function as the apertures for the passage of light, and, when the discs are superposed on each other with these sides facing toward one another, they also may define at least one compartment for placing gel therein.

This embodiment makes it possible to improve the operational capabilities of the apparatus, namely, to scan gels having a different cross-sectional configuration, e.g., rectangular configuration.

The provision of this capability in the apparatus according to the invention is very important as electrophoretic analysis in gel plates has recently come into a widespread use. In such case, the scanning is conducted after cutting individual electrophoretic samples from the plate.

The grooves of the cell discs are preferably made along the perimeter of each disc.

This embodiment of the cell makes it possible to substantially simplify the apparatus since a simple and cheap electromechanical drive may be used for causing the cell to move relative to the light beam from the monochromator.

The apparatus is preferably provided with a bath filled with a liquid having a refractive index similar to that of the gel material, the bath having optically transparent inlet and outlet windows for the light beam and being installed between the stop aperture and the photometer in such a manner that the part of the cell discs having compartments for placing gels therein should be submerged in the bath liquid.

This facility makes it possible to substantially reduce the light diffusion and influence of surface damages to gels on the scanning results. As a consequence of this, the apparatus according to the invention has an improved sensitivity in measurements as a result of a lower background of light diffusion, and the amplitude of false peaks in the scanning record caused by surface damages to gels is substantially lowered.

BRIEF DESCRIPTION OF THE DRAWINGS

The invention will now be described in detail with reference to specific embodiments illustrated in the accompanying drawings, in which:

FIG. 2 is a plan view of the inside surface of one of the discs of a call of the apparatus shown in FIG. 1;

FIG. 4 is a longitudinal section of a part of the cell discs of another embodiment of the apparatus according to the invention; and FIG. 5 is the same as FIG. 4, but with the discs superposed on one another with their opposite sides.

DETAILED DESCRIPTION OF THE INVENTION

Figure 1:
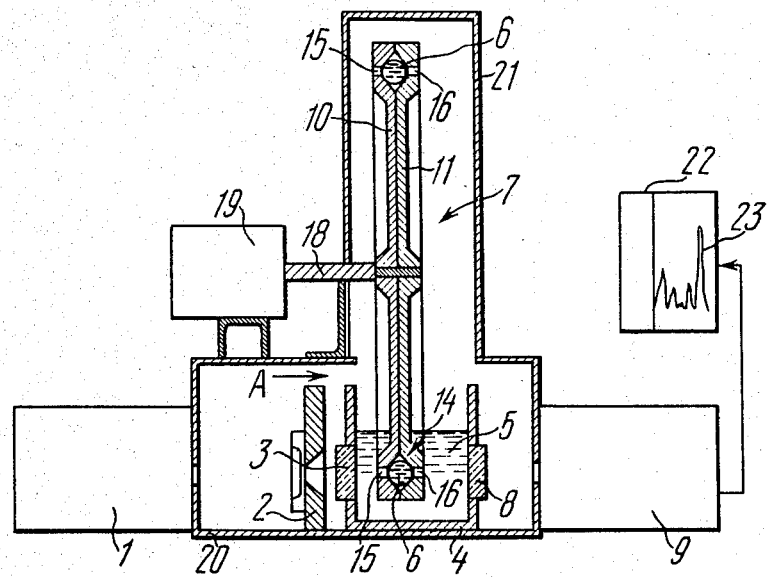
FIG. 1 is an elevational view, partially in longitudinal section, of an apparatus for photometrically scanning gels according to the invention.

An apparatus for photometrically scanning gels according to the invention comprises a monochromator 1 (FIG. 1) from which the light beam passes through a stop aperture 2, an inlet optically transparent window 3 of a bath 4 filled with a liquid 5, a gel 6 placed in a cell 7, and an outlet optically transparent window 8 of the bath 4, which are disposed one after the other along the path of the light beam, the light being received by a photometer 9.

The cell 7 is made in form of two superposed discs 10, 11 made of a metal, e.g., of an aluminium alloy, which have on their inside surfaces 12 (FIG. 2) congruent grooves 13.

The grooves 13 of the discs 10, 11 are made along the perimeter of the discs.

Various embodiments of the apparatus may be used with several grooves differently spaced from the center of the discs or even with a single spiral groove.

When the discs 10 and 11 (FIG. 1) are superposed on one another, the grooves 13 (FIG. 2) define a compartment 14 (FIG. 1) for placing gels 6 therein. In this embodiment of the apparatus a single compartment 14 is defined in which four gels 6 are placed.

The apparatus may be made with the discs having several compartments.

Both discs 10, 11 have, on the side of the bottom of the grooves 13 (FIG. 2), apertures 15 and 16, respectively, for the passage of the light beam (FIG. 1). Bridges 17 are provided for the discs 10, 11 to remain integral.

Discs 10, 11 (FIG. 1) of the cell 7 are installed on an output shaft 18 of a drive 19 for rotation (movement) relative to the light beam.

By using washers of various thickness (not shown) placed between the two discs 10, 11 of the cell 7, the space between the discs 10 and 11 may be varied so as to change the cross-sectional dimensions of the compartment 14 thus making it possible to scan gels 6 over a wide range of their cross-sectional size.

As mentioned above, the bath 4 is filled with the liquid 5. The liquid is chosen so that its refractivity index should be similar to the refractivity index of the material of the gels 6. Thus, in this embodiment the liquid 5 is water as polyacrylamide or agar gels 6 are to be studied.

The bath 4 is installed between the stop aperture 2 and the photometer 9 in such a manner that the part of the discs 10, 11 of the cell 7 (FIG. 3) having the compartment 14 (FIG. 1) for placing the gels 6 is in the liquid 5.

Figure 3:
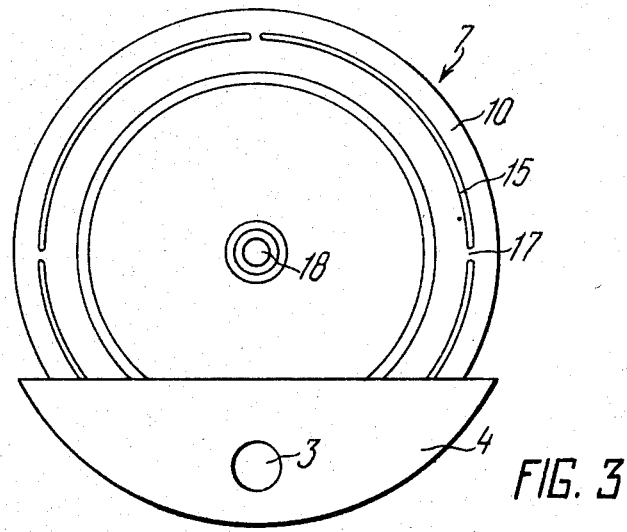
FIG. 3 is a view taken in the direction of arrow A in FIG. 1 showing a bath with a liquid in which is submerged a part of the cell discs of the apparatus of FIG. 1.

As it can be seen in FIG. 3, the bath 4 is in the form of a segment. This is determined by the configuration of the cell 7 and enables saving of the liquid when the liquid might contain expensive additives.

The stop aperture 2 (FIG. 1), the bath 4 and the cell 7 are accommodated in a housing 20 which has a removable light-protective hood 21. The hood 21 has an opening for the output shaft 18 of the drive 19 on which are removably installed the discs 10, 11 of the cell 7.

The output of the photometer 9 is electrically coupled to a recorder 22 having a chart sheet on which is recorded a scanning record 23 having peak which are used to assess the position of studied substances in the electrophoretic sample.

The embodiment of the apparatus according to the invention which has been described above, in which the compartment 14 defined by the grooves 13 upon superposing the discs 10 and 11 of the cell 7 on one another, is designed for scanning cylindrical gels 6.

However, by changing the configuration of the grooves, gels of different configuration may be scanned.

FIGS. 4 and 5 show the cell 7 of the apparatus according to the invention which is formed by superposing discs 24 and 25 having congruent grooves 26 and 27 on both one side 28 and an opposite side 29, respectively. This construction of the cell 7 enables its application for gels of different configurations.

Thus, in case the discs 24 and 25 of the cell 7 (FIG. 4) are superposed with their sides 28 facing toward one another, the grooves 26 define a compartment 30 for placing therein cylindrical gels 6, and the grooves 27 made on the outer side 29 of the discs 24, 25 function as apertures for the passage of light.

When the discs 24, 25 of the cell 7 (FIG. 5) are superposed with their sides 29 facing toward one another, the grooves 27 form a compartment 31 for placing therein gels 32 of a rectangular cross-sectional configuration, and the grooves 26 on the outer side 28 of the discs 24, 25 function as apertures for the passage of light.

There may be several commmpartments 31 and 32 (FIG. 4).

The apparatus for photometrically scanning gels according to the invention functions in the following manner.

After the removal of the light-protecting hood 21 (FIG. 1), both discs 10, 11 or both discs 24, 25 (FIG. 4) of the cell 7 (FIG. 1) are removed from the shaft 18 of the drive 19. The gels 6 or 32 are placed into the groove 13 or 26 (FIG. 4) or 27 (FIG. 5) of one of the discs 10 or 24 so that spaces of at least two-three millimeters should be left between the ends of the gels 6 and 32 and the bridges 17. Then the disc 11 or 25 is superposed so that both grooves 13, 26, 27 define the compartment 14, 30 for cylindrical gels 6 and compartment 31 for gels 32 of rectangular cross-sectional configuration, and that the bridges 17 of both discs 10, 11 or 24, 25 should be brought in register.

Water is poured into the bath 4 (FIG. 1) so that the water level should be slightly above the windows 3, 8. The assembled cell 7 with the gels 6 or 32 placed therein is put on the shaft 18 of the drive 19 so that the light beam from the monochromator 1 should be targeted to the aperture 15. Then the light-protecting hood 21 is installed, and the reference line of the photometer 9 is set-up. The drive 19 is turned on, a well as the chart sheet transport drive of the recorder 22, and the photometric scanning of the gels 6 or 32 is conducted. The light beam from the monochromator 1 (FIG. 1) passes through the stop aperture 2 which cuts-out from the beam a narrow beam 0.2 mm wide passing, consecutively, through the inlet window 3 of the bath 4, the water, the aperture 15, the gel 6, the aperture 16, the water, the outlet window 8 of the bath 4 and is incident upon the photometer 9. The absorption of the light beam passing through the gel 6 is recorded by the recorder 22. The points of location of the zones of the biological substance being analyzed in the gels are recorded by the recorder as peaks on the scanning record 23. After the discs of the cell 7 have performed a complete revolution, the scanning process is terminated. Scanning the gel 32 (FIG. 5) of the rectangular cross-sectional configuration is performed in the similar manner.

For placing into the cell gels of a size greater than the cross-sectional size of the compartment, washers of a thickness sufficient for fixing the gels are placed between the discs.

In a specific application of the apparatus according to the invention, a consecutive scanning of four, e.g., cylindrical gels each 12 cm long or one gel 50 cm long is possible without recharging the cell. The grooves in the discs of the cell are made with a 17 cm diameter. As the width of the light beam passing through the gel during the scanning is normally between 0.1 and 0.5 mm, the curvature of the gels along an arc of 17 cm in diameter does not affect the accuracy of measurement.

The application of the apparatus according to the invention makes it possible, the other conditions being equal, to improve the accuracy of scanning gels by 1.5–2 times, to obtain a 3–4-fold reduction of the number of auxiliary operations and to lower the cost of the apparatus by a quarter.

INDUSTRIAL APPLICABILITY

The apparatus for photometrically scanning gels according to the invention may be used in clinics and at microbiological factories for conducting mass-scale tests with the quantitative evaluation of electrophoretic patterns in gels, e.g., in polyacrylamide and agar gels, as well as for conducting selective operations in agriculture.

I claim:

1. An apparatus for photometrically scanning gels, comprising a monochromator from which a light beam passes through a stop aperture and a gel placed in a cell, which are installed one after the other along the path of the light beam, the cell being caused to move relative to the light beam by means of an electromechanical drive and the light being received by a photometer, wherein the improvement comprises the cell comprising two superposed discs each having on at least one side thereof congruent grooves which define at least one compartment for placing gels therein when the discs are superposed on one another.

2. An apparatus according to claim 1, wherein both discs of the cell have apertures in a surface opposite to the surface in which the groove is defined and in line with the bottom of the grooves for the passage of light.

3. An apparatus according to claim 2, wherein grooves are made on both sides of the discs of the cell, the grooves made on the opposite side of the discs of the cell function as apertures for the passage of light, and, when the discs are superposed on one another with these sides facing toward one another, they also define at least one compartment for placing gels.

4. An apparatus according to claim 1 wherein the grooves of the discs of the cell are made along the perimeter of the discs.

5. An apparatus according to any claim 1 through 4, further comprising a bath filled with a liquid having a refractivity index similar to the refractivity index of the material of the gels, the bath having an optically transparent inlet window and an outlet window for the passage of light beam and being installed between the stop aperture and the photometer, the part of the discs of the cell having the compartment for placing the gels therein being submerged in the bath liquid.

* * * * *